(12) United States Patent
Fritsch et al.

(10) Patent No.: US 6,308,359 B2
(45) Date of Patent: *Oct. 30, 2001

(54) BRUSH SECTION FOR AN ELECTRIC TOOTHBRUSH

(75) Inventors: Thomas Fritsch, Eppstein; Hansjörg Reick, Kronberg, both of (DE)

(73) Assignee: Braun GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/842,565

(22) Filed: Apr. 26, 2001

Related U.S. Application Data (63) Continuation of application No. 09/506,152, filed on Feb. 17, 2000, which is a continuation of application No. PCT/EP98/04750, filed on Jul. 30, 1998.

(30) Foreign Application Priority Data

Oct. 17, 1997 (DE) ............................................. 197 45 876

(51) Int. Cl.⁷ .......................... A61C 17/34; A46B 13/02
(52) U.S. Cl. ................. 15/22.1; 15/28; 403/313; 403/314; 403/326; 403/377
(58) Field of Search .............................. 15/28, 22.1, 22.2, 15/22.3, 22.4, 23, 29, 24; 403/313, 314, 326, 374, 377

(56) References Cited

U.S. PATENT DOCUMENTS

| | | | |
|---|---|---|---|
| 3,183,538 | 5/1965 | Hübner | 15/22 |
| 3,195,537 | 7/1965 | Blasi | 128/56 |
| 3,220,039 | 11/1965 | Dayton et al. | 15/28 |
| 3,939,599 | 2/1976 | Henry et al. | 32/59 |
| 4,156,620 | 5/1979 | Clemens | 134/6 |
| 4,827,550 | 5/1989 | Graham et al. | 15/22 |
| 4,827,552 | 5/1989 | Bojar et al. | 15/28 |
| 4,989,287 | 2/1991 | Scherer | 15/22.1 |
| 5,054,149 | 10/1991 | Si-Hoe et al. | 15/28 |
| 5,289,604 | 3/1994 | Kressner | 15/22.1 |
| 5,359,747 | 11/1994 | Amakasu | 15/22.1 |
| 5,461,744 | 10/1995 | Merbach | 15/22.1 |
| 5,625,916 | * 5/1997 | McDougall | 15/28 |

FOREIGN PATENT DOCUMENTS

| | | | |
|---|---|---|---|
| 368 780 | 6/1963 | (CH) | 9/5 |
| 1 212 036 | 3/1966 | (DE) . | |
| 1 299 056 | 6/1962 | (FR) . | |
| 477799 | 1/1938 | (GB) | 15/28 |
| 53-21650 | 2/1978 | (JP) | A46B/13/02 |
| WO91/07117 | 5/1991 | (WO) | A46B/13/02 |

OTHER PUBLICATIONS

Color photographs of Bausch & Lomb "Interplak" Model PB–4B style Handpiece with travel protection switch and Toothbrush attachment (handpiece stamped "1D IA", believed circa 1992 on sale in the United States) (7 views).
Package rear and bottom panels of Bausch & Lomb Interplak Model PB–4B, marked © 1990 (color copy, 1 sheet).
Product use instructions to Bausch & Lomb Interplak travel–style "Voyager" model TK–2 marked © 1991 (6 photocopied sheets containing cover and pp. 1–10).
Color photographs of Bausch & Lomb "Inteplak" Model PB–6 style Handpiece with waterproof electronic travel protection switch (believed circa 1992 on sale in the United States) (6 views).
Package rear and bottom panels of Bausch & Lomb Interplak Model PB–6, marked © 1992 (color copy, 1 sheet).

\* cited by examiner

*Primary Examiner*—Gary K. Graham
(74) *Attorney, Agent, or Firm*—Edward S. Podszus (57) ABSTRACT

The invention is directed to a brush section (2) for an electric toothbrush (1), having a carrier tube (4) to which is fitted a bristle carrier (5) comprising a plurality of bristles (6). The carrier tube (4) is adapted to plug onto a mount (7) of a hand piece (3) of the electric toothbrush (1). Provision is made for spring elements (14) arranged between the carrier tube (4) and the mount (7). Noises and vibrations are thereby reduced when the electric toothbrush (1) is in the activated condition.

68 Claims, 3 Drawing Sheets

BRUSH SECTION FOR AN ELECTRIC TOOTHBRUSH

This application is a continuation of application U.S. Ser. No. 09/506,152, filed on Feb. 17, 2000, now allowed, which is a continuation application of International Application PCT/EP98/04750, with an international filing date of Jul. 30, 1998.

This invention relates to a brush section for an electric toothbrush, having a carrier tube to which is fitted a bristle carrier comprising a plurality of bristles, and being adapted to plug onto a mount of a hand piece of the electric toothbrush. Further, the present invention relates to an electric toothbrush with a hand piece and a brush section of the aforementioned type.

A brush section of this type and an electric toothbrush of this type are generally known and commercially available.

An electric motor and a storage battery are accommodated in the hand piece of the electric toothbrush. The bristle carrier held on the brush section is mounted on the carrier tube for rotary or pivotal motion. When the toothbrush is activated, a rotary motion produced by the electric motor is transmitted to the bristle carrier by way of suitable shafts and joints. Hence the bristles are made to perform a cleaning movement. The bristles can be placed by a user against the surface of his teeth and thus used for dental care.

In the course of time the bristles of the brush section become worn and have to be replaced. It is partly for this reason that the brush section is designed to be plugged on the hand piece because then it can be replaced. The carrier tube of the brush section and the mount of the hand piece are coordinated to be joinable together by positive engagement. In this manner the brush section is fixedly held on the hand piece in a positive-engagement relationship thereto.

Plugging on the brush section and, in particular, pulling it off the hand piece should not require too much force of the user. This is why, as previously mentioned, provision is only made for a positive-engagement relationship between the carrier tube and the mount. A press-fit connection or the like is not possible. Consequently, the carrier tube and the mount usually display a certain play.

When the electric toothbrush is activated this play results in a movement which is oriented particularly in a radial direction but also partly in a tangential direction. This movement creates undesirable noises and vibrations of the brush section relative to the hand piece. Furthermore, said movement makes it at least more difficult for optimum transmission of the cleaning movement to the surface of the teeth.

It is an object of the present invention to devise a brush section for an electric toothbrush such that it enables a zero-play connection with the hand piece yet does not require greater force of the user when plugging on or pulling off the brush section.

This object is accomplished with a brush section of the type initially referred to by providing spring elements arranged between the carrier tube and the mount.

The spring elements ensure that the carrier tube and hence the brush section adopts a zero-play position on the mount and hence on the hand piece. Undesirable movements of the brush section in the activated state are thus reliably prevented, as are the noises and vibrations resulting therefrom. At the same time the spring elements require no special force of the user when plugging the brush section on the hand piece. On account of the resilient characteristics of the spring elements the user has to overcome only a small resistance in order to urge back the spring elements and plug the carrier tube on the mount. Overcoming this resistance signifies no great effort and hence no reduction of comfort for the user but is taken rather as a sign that the brush section is now plugged correctly on the hand piece. Thanks to the spring elements the brush section is fixedly held on the mount of the hand piece in such a way that no relative movements arise between the profiled sleeve and the mount when the brush head is pressed (or better placed) against the surface of the teeth and when only small contact forces are applied. It is thereby ensured that even smallest movements of the mount are invariably transmitted to the mouthpiece.

In an advantageous further aspect of the present invention the spring elements are either fitted to the brush section or are fitted to the hand piece and/or the mount and/or are adapted to plug onto the mount. The spring elements can thus be assigned to the component best suited for design reasons for implementation of the same. This may be not only the brush section but also the hand piece and particularly its mount. Similarly, it is possible to design the spring elements as a separate component to be plugged on the hand piece and/or the mount.

If the spring elements are assigned to the brush section, provision is made in a first advantageous embodiment of the invention for a sleeve equipped with the spring elements and adapted to plug into the carrier tube. Hence with a view to the material selection, for example, the spring elements can be manufactured independently of the other components of the brush section. Similarly, the spring elements can be constructed with an optimum design for their intended function, without having to make allowance for any particular fringe conditions of the brush section's other components.

If the spring elements are assigned to the brush section, provision is made in a second advantageous embodiment of the invention for the carrier tube to be equipped with the spring elements. No separate component is needed, therefore, to implement the spring elements. Instead the spring elements are integrated in the carrier tube. This represents a particularly simple and convenient way to accommodate the spring elements, particularly with a view to the material outlay and production effort required.

In an advantageous further aspect of the present invention, the sleeve or the carrier tube includes as spring elements at least one shoulder having a bend that curves in the direction of the mount. The spring elements are thus implemented by means of one or several curved shoulders. This shoulder ultimately forms a type of bending bar whose curvature results in the desired resilient characteristics. Starting from the sleeve plugged onto the carrier tube or from the carrier tube the curve is oriented in the direction of the hand piece mount. When the mount is inserted in the carrier tube, the curve is oriented inwards. A certain resistance develops on the curve of the shoulder which the user is in a position to overcome using a slight pressing motion. The resilient characteristics of the shoulder then act on the brush section in such a way that it is held in the mount without play.

Particularly conveniently, the sleeve or the carrier tube is made of a plastics material. The shoulder is thus also made of plastic so that the plastic's capability of being bent has an advantageous effect on the resilient properties of the shoulder.

Further features, application possibilities and advantages of the present invention will become apparent from the subsequent description of embodiments of the invention illustrated in the Figures of the accompanying drawing. It will be understood that any single feature and any combination of single features described or represented by illustration form the subject-matter of the present invention, irrespective of their summary in the patent claims or their back reference, as well as irrespective of their wording and representation in the description and the drawing, respectively.

DETAILED DESCRIPTION OF PREFERRED EMBODIMENTS

Figure 1:
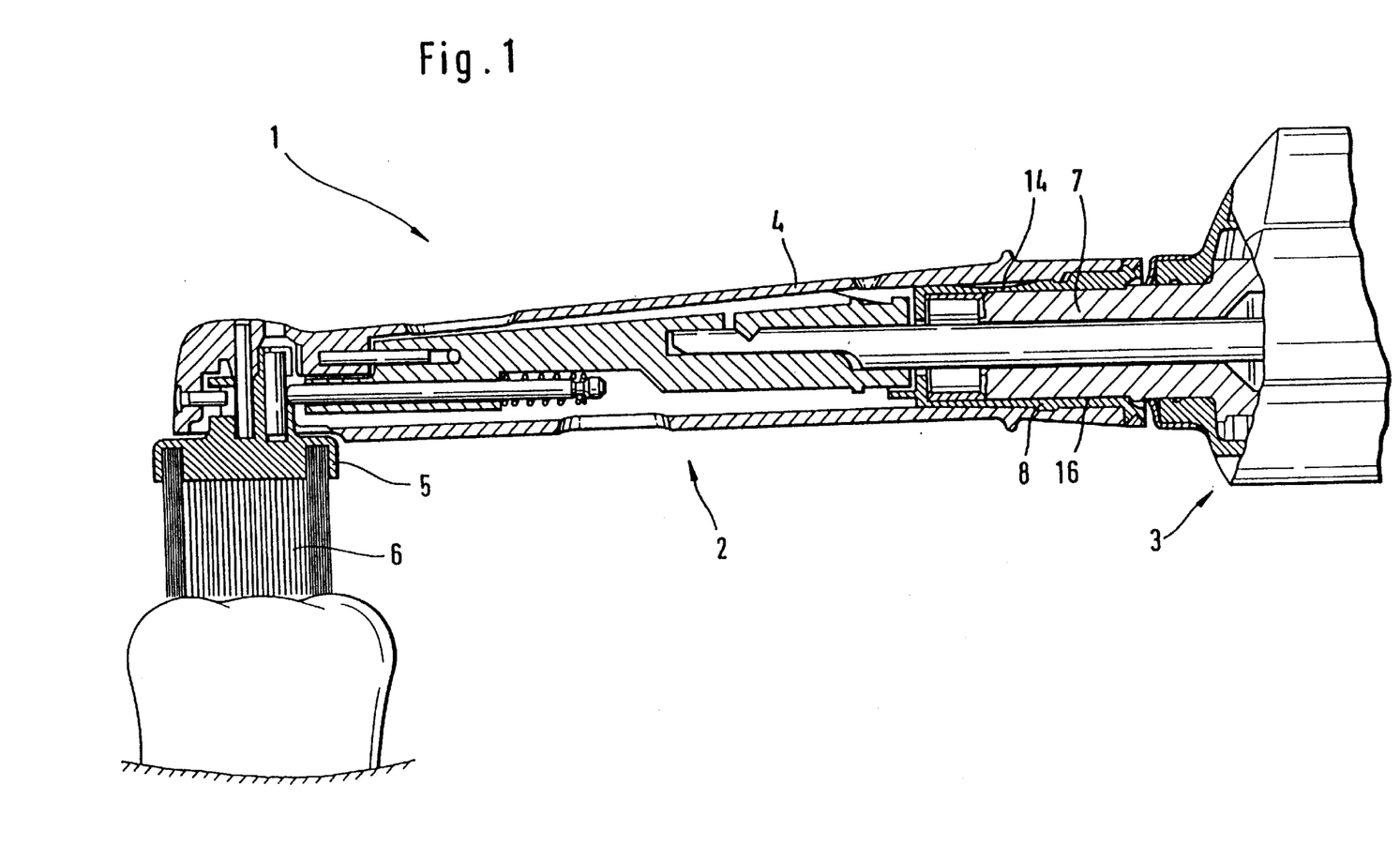
FIG. 1 is a schematic longitudinal sectional view of a brush section for an electric toothbrush illustrating an embodiment of the present invention.

FIG. 1 shows an electric toothbrush 1 having a brush section 2 and a hand piece 3. The brush section 2 is plugged on the hand piece 3 but can be pulled off the hand piece 3 in order, for example, to be replaced by a different brush section 2.

The brush section 2 has an elongate carrier tube 4 with a bristle carrier 5 projecting at approximately right angles from 43 the tube end remote from the hand piece 3. The bristle carrier 5 is equipped with a plurality of bristles 6. At its end close to the brush section 2 the hand piece 3 has a mount 7 on which the brush section 2 is plugged.

Further accommodated in the hand piece 3 are an electric motor and a storage battery. With the electric toothbrush 1 activated, a rotary or pivotal motion produced by the electric motor is transmitted by means of shafts, couplings, gears and the like to the bristle carrier 5 which thus performs a rotary or pivotal motion about an axis approximately parallel to the bristles 6.

With the electric toothbrush 1 actuated, a user can place the bristles 6 against the surfaces of his teeth and use the rotary or pivotal motion of the bristle carrier 5 to clean and care for his teeth.

A sleeve 8 is provided in the end of the brush section 2 close to the hand piece 3. In this area of the brush section 2 the carrier tube 4 is of an approximately cylindrical configuration and the sleeve 8 is plugged in the carrier tube 4. The sleeve 8 is secured against rotary movement in the carrier tube 4 as by ridges or the like engaging in grooves. Furthermore, the sleeve 8 is secured against being pulled out of the carrier tube 4 by detent elements or the like.

Figure 2A:
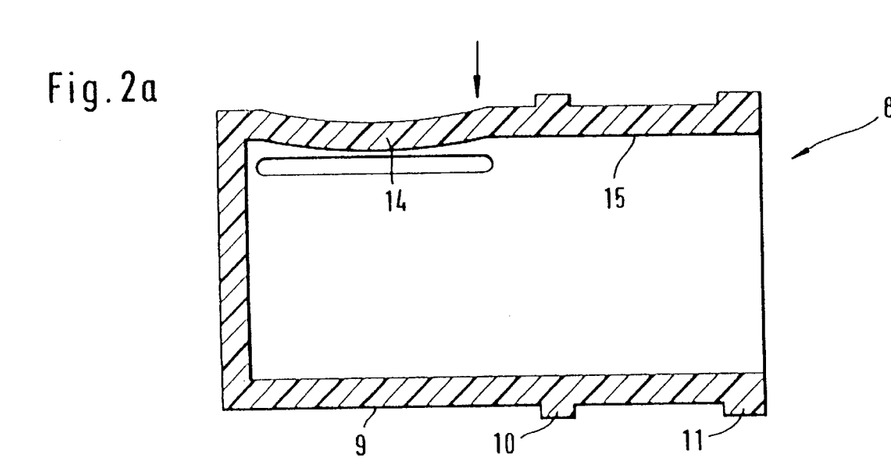
FIGS. 2a to 2c represent schematically a longitudinal sectional view, a top plan view and a cross-sectional view, respectively, of a sleeve of the brush section of FIG. 1.
Figure 2B:
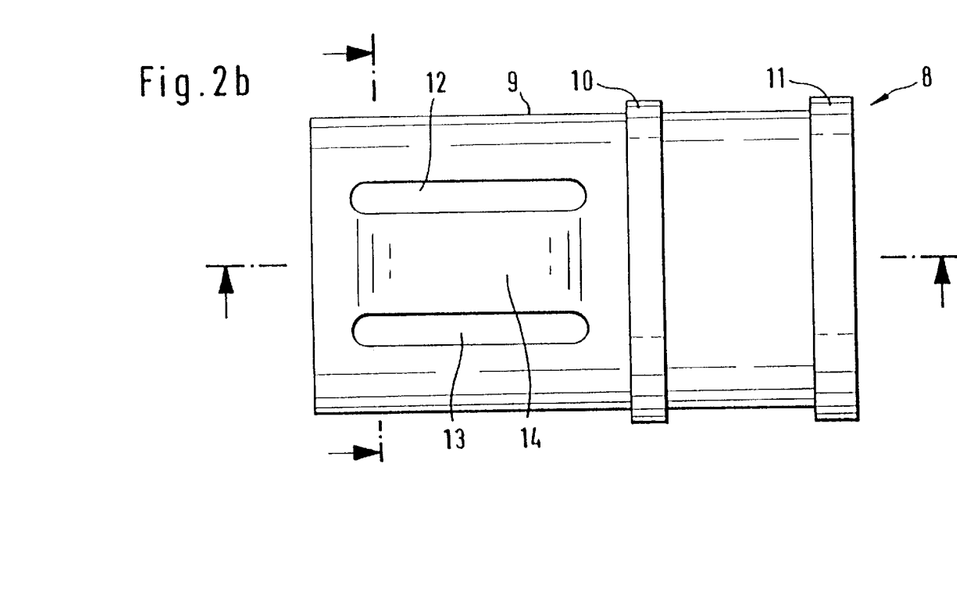
Figure 2C:
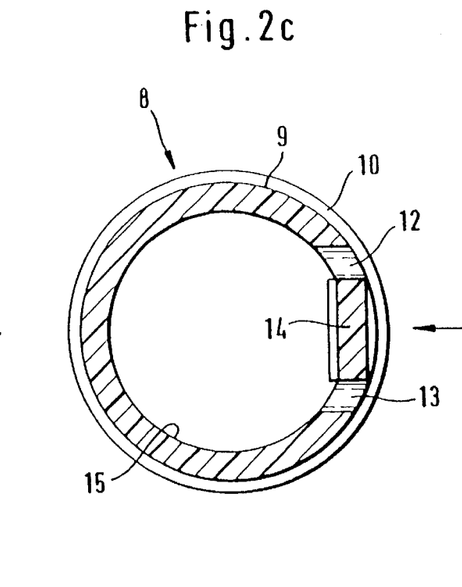

FIGS. 2a to 2c show the sleeve 8 of the brush section 2 on an enlarged scale.

The sleeve 8 is of a cylindrical construction and has an essentially circular cross section. On its outside wall 9 the sleeve 8 has two circumferential annular ridges 10, 11, at least one of which can act as detent element.

In the longitudinal direction the sleeve 8 has two slots 12, 13, with a shoulder 14 constructed in between. As can be seen in FIG. 2a in particular, the shoulder 14 is equipped with a curve or bend. The latter is oriented inwards, meaning toward the smaller diameters, and hence in the direction of the mount 7 of the hand piece 3.

At least the shoulder 14 is made of a flexible or elastic material. The entire sleeve 8 in particular is made of a plastics material. The shoulder 14 thus forms a bending bar with resilient properties. Hence the shoulder 14 performs the function of spring elements.

The inside wall 15 of the sleeve 8 has a cross-sectional shape and a diameter conforming to the outside wall 16 of the mount 7 so that the mount 7 can be plugged in the sleeve 4 by positive engagement therewith. Where applicable, the sleeve 8 and the mount 7 have cross sectional shapes designed to permit the sleeve 8 and hence the brush section 2 to be plugged on the mount 7 and hence on the hand piece 3 only when turned to a certain position.

To plug the brush section 2 on the hand piece 3, the mount 7 of the hand piece 3 has to be inserted in the sleeve 8 of the brush section 2. As this occurs, the sleeve 8 is itself plugged in the carrier tube 4 of the brush section 2. When the mount 7 reaches the inward projecting bend of the shoulder 14, a certain resistance results. This resistance is overcome by pressing back the bend of the shoulder 14. The mount 6 can then be inserted fully in the sleeve 8. The brush section 2 is thus plugged fully on the hand piece 3.

Figure 2D:
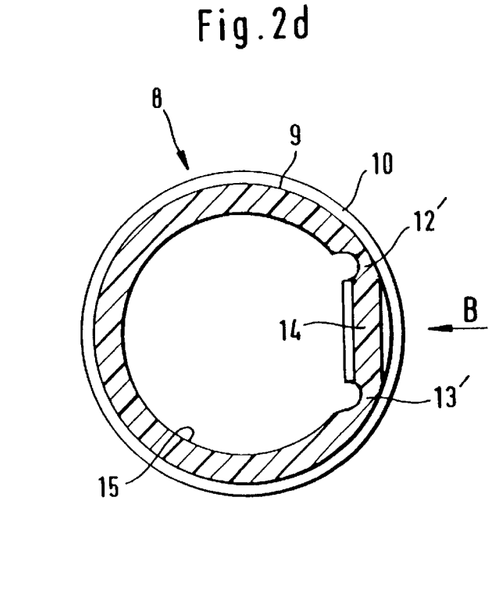
FIGS. 2d to 2f represent alternate embodiments in various views of the sleeve of the brush section.
Figure 2E:
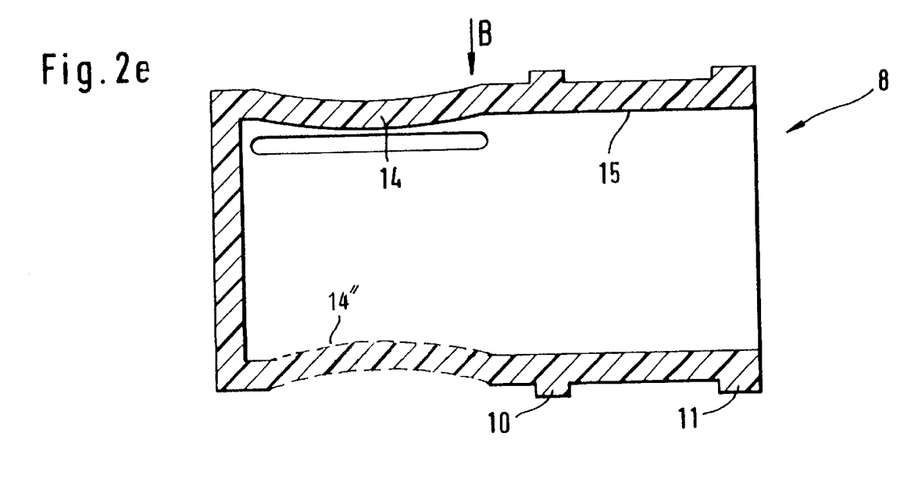
Figure 2F:
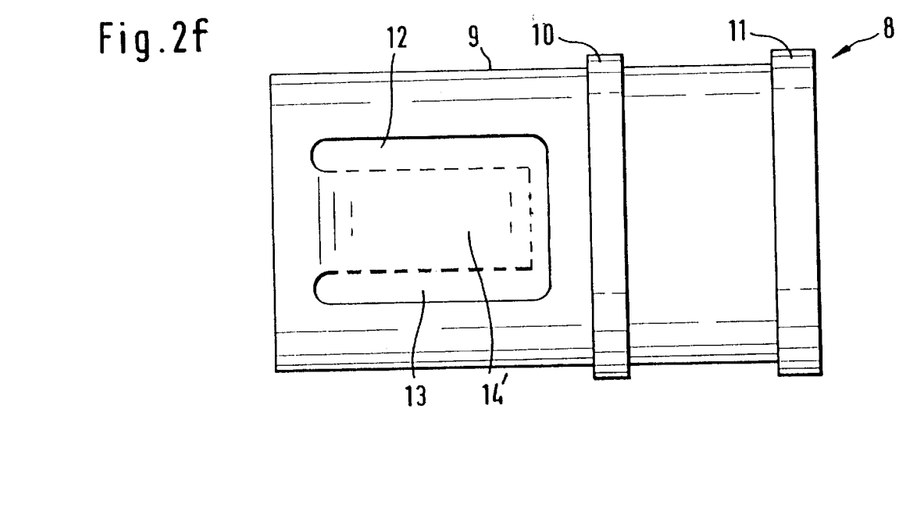

In a configuration differing from the sleeve 8 as described, there can be either two or more shoulders 14 and 14". The shoulder or shoulders 14 do not have to be fastened at both ends (see 14'); it is also possible for the shoulder or shoulders 14 to be fixed at one end only (14'). The slots 12, 13 defining the shoulder or shoulders 14 may also be implemented by reductions in wall thickness (12', 13') to the sleeve 8 so that the sleeve is completely closed around its circumference. It is also possible for the spring elements to be incorporated generally in the sleeve 8 as elastic components in the broadest sense.

It is likewise possible for the spring elements to be arranged directly on the carrier tube 4, thereby eliminating the need for the sleeve 8. This can be accomplished, for example, by providing the shoulder or shoulders 14 directly on the carrier tube 4. At least the shoulder or shoulders 14, or the complete carrier tube 4 as well, are then made particularly of a plastics material, thus producing the desired resilient characteristics.

Another possibility is for the spring elements to be assigned to the hand piece 3 and not to the brush section 2. In this arrangement the spring elements can be provided directly on the hand piece 3 or on the mount 7. Similarly it is possible for the spring elements, for example, in the form of a sleeve or the like, to be plugged on the mount 7.

Further, the spring elements can be constructed so that they produce not only a force outwards in a radial direction but also a force in a tangential direction. This enables tangential movements of the brush section in the activated state to be prevented and vibrations and noises to be further reduced.

We claim:

1. A replaceable brush section for an electric toothbrush hand piece having a mount at one end thereof and a drive shaft rotationally disposed within the mount and protruding outwards thereof, said brush section comprising a plastic carrier tube to which is fitted a bristle carrier comprising a plurality of teeth-cleaning bristles, said bristle carrier moveable for rotation relative the carrier tube, a longitudinal axle rotationally disposed within the carrier tube and drivingly connected to the bristle carrier and adapted to be coupled to the rotary drive shaft of the hand piece, and said carrier tube adapted to push onto the mount of the hand piece of the electric toothbrush in radially surrounding relation to the mount, and at least one resilient element formed of plastic and attached to the brush section and which is arranged between a radially inwardly directed surface of the carrier tube and a confronting radially outwardly directed surface of the mount, wherein the resilient element biasingly bears against the mount surface thereby frictionally hindering inadvertent motion of the carrier tube relative the mount.

2. The brush section of claim 1, wherein the resilient element is disposed on a wall of the carrier tube.

3. The brush section of claim 1, wherein the resilient element is configured as a sleeve received within the carrier tube.

4. The brush section of claim 3, wherein at least one of the sleeve and the carrier tube comprises at least one radially inwardly directed shoulder forming said at least one resilient element, said at least one shoulder having a camming surface extending in the direction of the mount.

5. The brush section of claim 1 in combination with an electric toothbrush hand piece.

6. The brush section of claim 1, wherein said resilient element extends longitudinally approximately parallel the carrier tube longitudinal axle.

7. The brush section of claim 1, wherein the outwardly directed surfaces of the mount have a cross sectional shape for receiving the brush section at only a predetermined angular orientation about the drive shaft extending through mount, and the inwardly directed surfaces of the brush section shaped to cooperate with the outwardly directed surfaces to attach said brush section to said mount at the predetermined orientation.

8. The brush section of claim 1, wherein the resilient element is defined adjacent a localized region of a reduced wall thickness formed in the carrier tube adjoining a neighboring remaining portion of the carrier tube having a non-reduced wall thickness.

9. The brush section of claim 1, wherein the resilient element is defined by a localized region of a wall of the brush section having a thickness differing from and adjoining a wall thickness of a remaining portion of the brush section more remote from the resilient element.

10. The brush section of claim 9, wherein the differing wall thickness is a reduced thickness.

11. The brush section of claim 1, wherein the resilient element has a radially inwardly directed free surface defining a distributed area contact face adapted to make distributed area contact generally parallel the longitudinal axle with a generally smooth surface of the radially outwardly directed lateral surface of the mount.

12. The brush section of claim 1, wherein the brush section longitudinal axle is disposed for oscillatory rotational motion within the carrier tube to effect oscillatory rotational motion of said bristle carrier.

13. A replaceable brush section for an electric toothbrush hand piece having a mount at one end thereof and a drive shaft rotationally disposed within the mount and protruding outwards thereof, said brush section comprising a plastic carrier tube to which is fitted a bristle carrier comprising a plurality of teeth-cleaning bristles, said bristle carrier moveable for rotation relative the carrier tube, a longitudinal axle rotationally disposed within the carrier tube and drivingly connected to the bristle carrier and adapted to be coupled to the rotary drive shaft of the hand piece, and said carrier tube adapted to push onto the mount of the hand piece of the electric toothbrush in radially surrounding relation to the mount, and at least one resilient element formed of plastic end attached to the brush section and which is arranged between a radially inwardly directed surface of the carrier tube and a confronting radially outwardly directed surface of the mount, wherein the resilient element bears against the mount surface thereby frictionally hindering inadvertent motion of the carrier tube relative the mount, and further comprising a sleeve on which is disposed the at least one resilient element, said sleeve adapted to be inserted onto the carrier tube.

14. The brush section of claim 13, wherein said sleeve is made of a plastics material.

15. The brush section of claim 14, wherein said resilient element is molded integrally with the sleeve.

16. The brush section of claim 15, wherein the resilient element is made of elastic material molded with the sleeve.

17. The brush section of claim 13, wherein the resilient element is defined adjacent a region of a reduced wall thickness formed in the sleeve.

18. A replaceable brush section for an electric toothbrush hand piece having a mount at one end thereof and a drive shaft rotationally disposed within the mount and protruding outwards thereof, said brush section comprising a plastic carrier tube to which is fitted a bristle carrier comprising a plurality of teeth-cleaning bristles, said bristle carrier moveable for rotation relative the carrier tube, a longitudinal axle rotationally disposed within the carrier tube and drivingly connected to the bristle carrier and adapted to be coupled to the rotary drive shaft of the band piece, and said carrier tube adapted to push onto the mount of the hand piece of the electric toothbrush in radially surrounding relation to the mount, and at least one resilient element formed of plastic and attached to the brush section and which is arranged between a radially inwardly directed surface of the carrier tube and a confronting radially outwardly directed surface of the mount, wherein the resilient element bears against the mount surface thereby frictionally hindering inadvertent motion of the carrier tube relative the mount, wherein the resilient element is deflectable relative the carrier tube upon plugging the brush section onto the mount.

19. The brush section of claim 18, wherein the resilient element is deflectable relative an outerwall surface of the carrier tube.

20. The brush section of claim 18, wherein the resilient element is deflectable relative an innerwall surface of the carrier tube.

21. A replaceable brush section for an electric toothbrush hand piece having a mount at one end thereof and a drive shaft rotationally disposed within the mount and protruding outwards thereof, said brush section comprising a plastic carrier tube to which is fitted a bristle carrier comprising a plurality of teeth-cleaning bristles, said bristle carrier moveable for rotation relative the carrier tube, a longitudinal axle rotationally disposed within the carrier tube and drivingly connected to the bristle carrier and adapted to be coupled to the rotary drive shaft of the hand piece, and said carrier tube adapted to push onto the mount of the hand piece of the electric toothbrush in radially surrounding relation to the mount, and at least one resilient element formed of plastic and attached to the brush section and which is arranged between a radially inwardly directed surface of the carrier tube and a confronting radially outwardly directed surface of the mount, wherein the resilient element bears against the mount surface thereby frictionally hindering inadvertent motion of the carrier tube relative the mount, wherein the resilient element is constructed as a cantilever beam member.

22. The brush section of claim 21, wherein the cantilever beam member is defined between two slots formed in the brush section one on either side of the beam.

23. The brush section of claim 21, wherein said resilient cantilever beam has camming structure facing in a direction at least partially away from the bristle carrier and that is shaped and positioned to interact with corresponding mount structure to facilitate deflection of said cantilever beam.

24. A replaceable brush section for an electric toothbrush hand piece having a mount at one end thereof and a drive shaft rotationally disposed within the mount and protruding outwards thereof, said brush section comprising a plastic carrier tube to which is fitted a bristle carrier comprising a plurality of teeth-cleaning bristles, said bristle carrier moveable for rotation relative the carrier tube, a longitudinal axle rotationally disposed within the carrier tube and drivingly connected to the bristle carrier and adapted to be coupled to the rotary drive shaft of the hand piece, and said carrier tube adapted to push onto the mount of the hand piece of the electric toothbrush in radially surrounding relation to the mount, and at least one resilient element formed of plastic and attached to the brush section and which is arranged between a radially inwardly died surface of the carrier tube and a confronting radially outwardly directed surface of the mount, wherein the resilient element bears against the mount surface thereby fictionally hindering inadvertent motion of the carrier tube relative the mount, wherein said resilient element has camming structure facing in a direction at least partially away from the bristle carrier and that is shaped and positioned to interact with corresponding mount structure to facilitate deflection of said resilient element.

25. A replaceable brush section for an electric toothbrush hand piece having a mount at one end thereof and a drive shaft rotationally disposed within the mount and protruding outwards thereof, said brush section comprising a plastic carrier tube to which is fitted a bristle carrier comprising a plurality of teeth-cleaning bristles, said bristle carrier moveable for rotation relative the carrier tube, a longitudinal axle rotationally disposed within the carrier tube and drivingly connected to the bristle carrier and adapted to be coupled to the rotary drive shaft of the hand piece, and said carrier tube adapted to push onto the mount of the hand piece of the electric toothbrush in radially surrounding relation to the mount, and at least one resilient element formed of plastic and attached to the brush section and which is arranged between a radially inwardly directed surface of the carrier tube and a confronting radially outwardly directed surface of the mount, wherein the resilient element bears against the mount surface thereby frictionally hindering inadvertent motion of the carrier tube relative the mount, wherein the at least one resilient element comprises at least two resilient elements.

26. A replaceable brush section for an electric toothbrush having an output drive shaft extending outward from a hand piece and rotationally disposed therein, said brush section comprising a carrier tube to which is fitted a bristle carrier comprising a plurality of bristles and having a base region adapted to removably push onto a mount of the hand piece of the electric toothbrush whose said output drive shaft protrudes outward of the mount, the mount extending from the hand piece along an extension axis, the bristle crier being adapted to be set in rotational motion relative the carrier tube by the output drive shave, the base region defining a recess having inwardly directed side surfaces shaped to mate with outwardly directed surfaces of the mount, a longitudinal axle rotationally disposed within the carrier tube and extending between the bristle carrier and the base region and adapted to be coupled to the output drive shaft of the hand piece, wherein the outwardly directed surfaces of the mount have a cross sectional shape for receiving the brush section at only a predetermined angular orientation about the extension axis, and the inwardly directed surfaces of the brush section are shaped to cooperate with the outwardly directed surfaces to attach said brush section base region in surrounding relation to said mount at the predetermined orientation, and at least one spring element attached to the brush section and being arranged between a radially inwardly directed surface of the carrier tube and a confronting radially outwardly directed surface of the mount and biasing the carrier tube relative to the mount thereby engaging the carrier tube to the mount retarding inadvertent movement therebetween during use of the toothbrush.

27. The brush section of claim 26, wherein the spring element is disposed on a wall of the carrier tube.

28. The brush section of claim 26, wherein the spring element is configured as a sleeve received within the carrier tube.

29. The brush section of claim 28, wherein at least one of the sleeve and the carrier tube comprises at least one radially inwardly directed shoulder forming said at least one spring element, said at least one shoulder having a camming surface extending in the direction of the mount.

30. The brush section of claim 26, in combination with an electric toothbrush hand piece.

31. The brush section of claim 26, wherein said spring element extends longitudinally approximately parallel the carrier tube longitudinal axle.

32. The brush section of claim 26, wherein the at least one spring element comprises at least two spring elements.

33. The brush section of claim 26, wherein the spring element is defined adjacent a localized region of a reduced wall thickness formed in the carrier tube adjoining a neighboring remaining portion of the carrier tube having a non-reduced wall thickness.

34. The brush section of claim 26, wherein the spring element is defined by a localized region of a wall of the brush section having a thickness differing from and adjoining a wall thickness of a remaining portion of the brush section more remote from the spring element.

35. The brush section of claim 34, wherein the differing wall thickness is a reduced thickness.

36. The brush section of claim 26, wherein the spring element member has a radially inwardly directed free surface defining a distributed area contact face adapted to make distributed area contact generally parallel the longitudinal axle with a generally smooth surface of the radially outwardly directed lateral surface of the mount.

37. The brush section of claim 26, wherein the brush section longitudinal axle is disposed for oscillatory rotational motion within the carrier tube to effect oscillatory rotational motion of said bristle carrier.

38. The brush section of claim 1 or 26, wherein said plurality of bristles are grouped into a plurality of bristle tufts, said plurality of bristle tufts being distributed over a face of said bristle carrier, each said tuft comprising a respective portion of said plurality of bristles, and said bristle carrier and said plurality of tufts rotatable in unison relative the carrier tube.

39. A replaceable brush section for an electric toothbrush having an output drive shaft extending outward from a hand piece and rotationally disposed therein, said brush section comprising a carrier tube to which is fitted a bristle carrier comprising a plurality of bristles and having a base region adapted to removably push onto a mount of the hand piece of the electric toothbrush whose said output drive shaft protrudes outward of the mount, the mount extending from the hand piece along an extension axis, the bristle carrier being adapted to be set in rotational motion relative the carrier tube by the output drive shave, the base region defining a recess having inwardly directed side surfaces shaped to mate with outwardly directed surfaces of the mount, a longitudinal axle rotationally disposed within the carrier tube and extending between the bristle carrier and the base region and adapted to be coupled to the output drive shaft of the hand piece, wherein the outwardly directed surfaces of the mount have a cross sectional shape for receiving the brush section at only a predetermined angular orientation about the extension axis, and the inwardly directed surfaces of the brush section are shaped to cooperate with the outwardly directed surfaces to attach said brush section base region in surrounding relation to said mount at the predetermined orientation, and at least one spring element attached to the brush section and being arranged between a radially inwardly directed surface of the carrier tube and a confronting radially outwardly directed surface of the mount and bearing on the mount thereby engaging the carrier tube to the mount retarding inadvertent movement therebetween during use of the toothbrush, and further comprising a sleeve on which is disposed the at least one spring element, said sleeve adapted to be inserted onto the carrier tube.

40. The brush section of claim 39, wherein said sleeve is made of a plastics material.

41. The brush section of claim 40, wherein said spring element is molded integrally with the sleeve.

42. The brush section of claim 41, wherein the spring element is molded with the sleeve.

43. The brush section of claim 39, wherein the spring element is defined adjacent a region of a reduced wall thickness formed in the sleeve.

44. A replaceable brush section for an electric toothbrush having an output drive shaft extending outward from a hand piece and rotationally disposed therein, said brush section comprising a carrier tube to which is fitted a bristle carrier comprising a plurality of bristles and having a base region adapted to removably push onto a mount of the hand piece of the electric toothbrush whose said output drive shaft protrudes outward of the mount, the mount extending from the hand piece along an extension axis, the bristle carrier being adapted to be set in rotational motion relative the carrier tube by the output drive shave, the base region defining a recess having inwardly directed side surfaces shaped to mate with outwardly directed surfaces of the mount, a longitudinal axle rotationally disposed within the carrier tube and extending between the bristle carrier and the base region and adapted to be coupled to the output drive shaft of the hand piece, wherein the outwardly directed surfaces of the mount have a cross sectional shape for receiving the brush section at only a predetermined angular orientation about the extension axis, and the inwardly directed surfaces of the brush section are shaped to cooperate with the outwardly directed surfaces to attach said brush section base region in surrounding relation to said mount at the predetermined orientation, and at least one spring element attached to the brush section and being arranged between a radially inwardly directed surface of the carrier tube and a confronting radially outwardly directed surface of the mount and bearing on the mount thereby engaging the carrier tube to the mount retarding inadvertent movement between during use of the toothbrush, wherein the spring element is deflectable relative the carrier tube upon plugging the brush section onto the mount.

45. The brush section of claim 44, wherein the spring element is deflectable relative an outerwall surface of the carrier tube.

46. The brush section of claim 44, wherein the spring element is deflectable relative an innerwall surface of the carrier tube.

47. A replaceable brush section for an electric toothbrush having an output drive shaft extending outward from a hand piece and rotationally disposed therein, said brush section comprising a carrier tube to which is fitted a bristle carrier comprising a plurality of bristles and having a base region adapted to removably push onto a mount of the hand piece of the electric toothbrush whose said output drive shaft protrudes outward of the mount, the mount extending from the hand piece along an extension axis, the bristle carrier being adapted to be set in rotational motion relative the carrier tube by the output drive shave, the base region defining a recess having inwardly directed side surfaces shaped to mate with outwardly directed surfaces of the mount, a longitudinal axle rotationally disposed within the carrier tube and extending between the bristle carrier and the base region and adapted to be coupled to the output drive shaft of the hand piece, wherein the outwardly directed surfaces of the mount have a cross sectional shape for receiving the brush section at only a predetermined angular orientation about the extension axis, and the inwardly directed surfaces of the brush section are shaped to cooperate with the outwardly directed surfaces to attach said brush section base region in surrounding relation to said mount at the predetermined orientation, and at least one spring element attached to the brush section and being arranged between a radially inwardly directed surfaces of the carrier tube and a confronting radially outwardly directed surface of the mount and bearing on the mount thereby engaging the carrier tube to the mount retarding inadvertent movement therebetween during use of the toothbrush, wherein the spring element is constructed as a cantilever beam member.

48. The brush section of claim 47, wherein the cantilever beam member is defined between two slots formed in the brush section one on either side of the beam.

49. The brush section of claim 47, wherein said cantilever beam has camming structure facing in a direction at least partially away from the bristle carrier and that is shaped and positioned to interact with corresponding mount structure to facilitate deflection of said cantilever beam.

50. A replaceable brush section for an electric toothbrush having an output drive shaft extending outward from a hand piece and rotationally disposed therein, said brush section comprising a carrier tube to which is fitted a bristle carrier comprising a plurality of bristles and having a base region adapted to removably push onto a mount of the hand piece of the electric toothbrush whose said output drive shaft protrudes outward of the mount, the mount extending from the hand piece along an extension axis, the bristle carrier being adapted to be set in rotational motion relative the carrier tube by the output drive shave, the base region defining a recess having inwardly directed side surfaces shaped to mate with outwardly directed surfaces of the mount, a longitudinal axle rotationally disposed within the carrier tube and extending between the bristle carrier and the base region and adapted to be coupled to the output drive shaft of the hand piece, wherein the outwardly directed surfaces of the mount have a cross sectional shape for receiving the brush section at only a predetermined angular orientation about the extension axis, and the inwardly directed surfaces of the brush section are shaped to cooperate with the outwardly directed surfaces to attach said brush section base region in surrounding relation to said mount at the predetermined orientation, and at least one spring element attached to the brush section and being arranged between a radially inwardly directed surface of the carrier tube and a confronting radially outwardly directed surface of the mount and bearing on the mount thereby engaging the carrier tube to the mount retarding inadvertent movement therebetween during use of the toothbrush, wherein said spring element has camming structure facing in a direction at least partially away from the bristle carrier and that is shaped and positioned to interact with corresponding mount structure to facilitate deflection of said spring element.

51. A brush section for an electric toothbrush having an output drive shaft ending from a hand piece, comprising a carrier tube to which is fitted a bristle carrier comprising a plurality of bristles and being adapted to plug onto a mount of the hand piece of the electric toothbrush whose said output drive shaft is moveable with respect to the mount, wherein at least one sprig element is attached to the brush section and is arranged between a radially inwardly directed surface of the carrier tube and a confronting radially outwardly directed surface of the mount and biases the carrier tube relative to the mount inhibiting relative movement therebetween during operation of the toothbrush and the plugged-on carrier tube is non-rotatable relative the mount.

52. The brush section of claim 51, wherein the at least one spring element is disposed on a wall of the carrier tube.

53. The brush section of claim 51 in combination with an electric toothbrush hand piece.

54. The brush section of claim 51, wherein the bristle carrier is adapted to be set in motion relative the carrier tube by the output drive shaft.

55. The brush section of claim 51, wherein the drive shaft extends through the mount and the carrier tube is formed in surrounding relation to the mount in a radial direction.

56. The brush section of claim 51, wherein the bristle carrier is rotatable relative the carrier tube, and further comprising a longitudinal axle rotationally disposed within the carrier tube and drivingly connected to the bristle carrier and adapted to be coupled to the hand piece output drive shaft when the carrier tube is plugged onto the mount.

57. The brush section of claim 56, wherein the brush section longitudinal axle is disposed for oscillatory rotational motion within the carrier tube to effect oscillatory rotational motion of said bristle carrier.

58. The brush section of claim 51, wherein the spring element has a radially inwardly directed free surface defining a distributed area contact face adapted to make distributed area contact, generally parallel a longitudinal axis of the carrier tube, with a generally smooth surface of the radially outwardly directed lateral surface of the mount.

59. The brush section of claim 51, wherein said plurality of bristles are grouped into a plurality of bristle tufts, said plurality of bristle tufts being distributed over a face of said bristle carrier, each said tuft comprising a respective portion of said plurality of bristles, and said bristle carrier and said plurality of tufts rotatable in unison relative the carrier tube.

60. The brush section of claim 51, wherein the outwardly directed surfaces of the mount have a cross sectional shape for receiving the brush section at a predetermined angular orientation about the mount, and the inwardly directed surfaces of the brush section cooperate with the outwardly directed surfaces to attach said brush section to said mount at the predetermined orientation.

61. The brush section of claim 51, wherein the spring element is constructed as a cantilever beam.

62. The brush section of claim 51, wherein the spring element is made of a plastics material.

63. A brush section for an electric toothbrush having an output drive shaft extending from a hand piece, comprising a carrier tube to which is fined a bristle carrier comprising a plurality of bristles and being adapted to plug onto a mount of the hand piece of the electric toothbrush whose said output drive shaft is moveable with respect to the mount, wherein at least one spring element is attached to the brush section and is arranged between a radially inwardly directed surface of the carrier tube and a confronting radially outwardly directed surface of the mount and frictionally engages the carrier tube to the mount inhibiting relative movement therebetween during operation of the toothbrush and the plugged-on carrier tube is non-rotatable relative the mount, and further comprising a sleeve on which is disposed the at least one spring element, said sleeve adapted to be inserted into the carrier tube.

64. The brush section of claim 63, wherein at least one of the sleeve and the carrier tube comprises at least one shoulder forming said at least one spring element, said at least one shoulder having a bend extending in the direction of the mount.

65. The brush section of claim 63, wherein said sleeve comprises a plastics material.

66. The brush section of claim 65, wherein said spring element is molded integrally with the sleeve.

67. The brush section of claim 66, wherein the spring element is made of elastic material molded with the sleeve.

68. A brush section for an electric toothbrush having an output drive shaft extending from a hand piece, comprising a carrier tube to which is fitted a bristle carrier comprising a plurality of bristles and being adapted to plug onto a mount of the hand piece of the electric tooth whose said output drive shaft is moveable with respect to the mount, wherein at least one spring element is attached to the brush section and is arranged between a radially inwardly directed surface of the carrier tube and a confronting radially outwardly directed surface of the mount and frictionally engages the carrier tube to the mount inhibiting relative movement therebetween during operation of the toothbrush and the plugged-on carrier tube is non-rotatable relative the mount, wherein the at least one spring element is deflectable relative the carrier tube upon plugging the brush section onto the mount.

* * * * *

UNITED STATES PATENT AND TRADEMARK OFFICE
CERTIFICATE OF CORRECTION

PATENT NO. : 6,308,359 B2
DATED : October 30, 2001
INVENTOR(S) : Fritsch et al.

It is certified that error appears in the above-identified patent and that said Letters Patent is hereby corrected as shown below:

Column 11,
Line 66, change "ending" to -- extending --;

Column 12,
Line 4, change "sprig" to -- spring --;
Line 56, change "fined" to -- fitted --; and Column 14,
Line 3, change "tooth" to -- toothbrush --.

Signed and Sealed this

Eighteenth Day of June, 2002

*Attest:*

*Attesting Officer*

JAMES E. ROGAN
*Director of the United States Patent and Trademark Office*